United States Patent
Clavel et al.

(10) Patent No.: US 6,881,848 B2
(45) Date of Patent: Apr. 19, 2005

(54) PROCESS FOR PREPARING 4-TRIFLUOROMETHYLSULFINYLPYRAZOLE DERIVATIVE

(75) Inventors: Jean-Louis Clavel, Ampuis (FR); Isabelle Pelta, Chassieu (FR); Sylvie Le Bars, Chuzelles (FR); Philippe Charreau, Sainte Foy les Lyon (FR)

(73) Assignee: BASF Agro B.V. Arnhem (NL), Wädenswil-Branch (CH)

( * ) Notice: Subject to any disclaimer, the term of this patent is extended or adjusted under 35 U.S.C. 154(b) by 0 days.

(21) Appl. No.: 10/611,979

(22) Filed: Jul. 3, 2003

(65) Prior Publication Data

US 2004/0034234 A1 Feb. 19, 2004

Related U.S. Application Data

(62) Division of application No. 10/111,000, filed as application No. PCT/EP99/08687 on Oct. 22, 1999, now Pat. No. 6,620,943.

(51) Int. Cl.$^7$ .............................................. C07D 231/10
(52) U.S. Cl. ................................. 548/366.1; 548/367.4
(58) Field of Search .......................... 548/366.1, 367.4, 548/364.1; 546/276.1

(56) References Cited

U.S. PATENT DOCUMENTS

| | | | |
|---|---|---|---|
| 5,082,945 A | 1/1992 | Wakselman et al. | |
| 5,232,940 A | 8/1993 | Hatton et al. | |
| 5,283,337 A | 2/1994 | Wakselman et al. | |
| 5,618,945 A | 4/1997 | Casado et al. | |

FOREIGN PATENT DOCUMENTS

| | | |
|---|---|---|
| EP | 0295117 A1 | 12/1988 |
| EP | 0374061 B1 | 6/1994 |
| EP | 0668269 A1 | 8/1995 |

OTHER PUBLICATIONS

Jean–Louis Clavel et al, *J. Chem. Soc. Perkin 1*, pp. 3371–3375 (1992), published by Chemical Society, London, England.

*Primary Examiner*—Golam M M Shameem
(74) *Attorney, Agent, or Firm*—Hutchison & Mason PLLC

(57) ABSTRACT

A process for the preparation of a compound of formula (I)

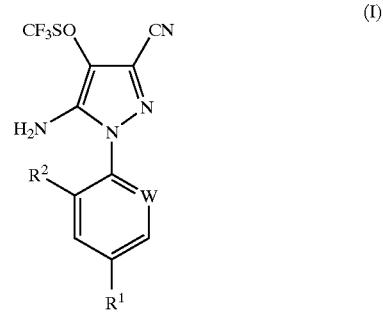

(I)

comprising oxidizing a compound of formula (II)

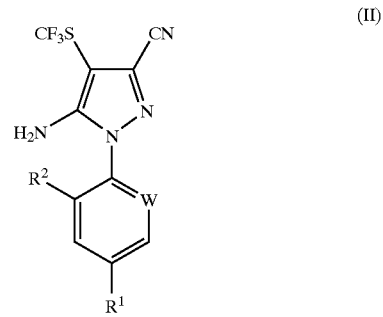

(II)

with trifluoroperacetic acid in the presence of a corrosion inhibiting compound such as boric acid. Also, a process for preparing a compound of formula (II) by adding sulfur dioxide to a mixture of the corresponding disulfide, a formate salt, trifluoromethyl bromide and a polar solvent; and a process for preparing the disulfide comprising adding $S_2Cl_2$ to a solution, in an organic solvent, of the corresponding 4-unsubstituted pyrazole.

41 Claims, No Drawings

PROCESS FOR PREPARING 4-TRIFLUOROMETHYLSULFINYLPYRAZOLE DERIVATIVE

CROSS-REFERENCE TO RELATED APPLICATIONS

This application is a divisional of Ser. No. 10/111,000 filed Aug. 15, 2002, now U.S. Pat. No. 6,620,943 which is a 371 of PCT/EP99/08687 filed Oct. 22, 1999.

This invention relates to improved processes for preparing 1-arylpyrazole pesticides such as 5-amino-1-(2,6-dichloro-4-trifluoromethylphenyl)-3-cyano-4-trifluoromethylsulfinylpyrazole known as Fipronil (Pesticide Manual 11th Edition), and for the intermediates used in its preparation 5-amino-1-(2,6-dichloro-4-trifluoromethylphenyl)-3-cyano-4-trifluoromethylthiopyrazole and 5-amino-1-(2,6-dichloro-4-trifluoromethylphenyl)-3-cyanopyrazol-4-yl disulfide.

European Patent Publication No.0295117 describes the preparation of 5-amino-1-(2,6-dichloro-4-trifluoromethylphenyl)-3-cyano-4-trifluoromethylsulfinylpyrazole by the oxidation of 5-amino-1-(2,6-dichloro-4-trifluoromethylphenyl)-3-cyano-4-trifluoromethylthiopyrazole with 3-chloroperbenzoic acid. The use of trifluoroacetic acid and hydrogen peroxide (forming trifluoroperacetic acid in situ) for the oxidation of sulfides to sulfoxides and/or sulfones is known and is generally useful for the oxidation of electron deficient sulfides such as trifluoromethylsulfides which are less readily oxidized than other sulfides. Such procedures have been reported in the literature, for example in the preparation of certain 1-arylpyrazole pesticides.

A problem encountered in the preparation of 5-amino-1-(2,6-dichloro-4-trifluoromethylphenyl)-3-cyano-4-trifluoromethylsulfinylpyrazole by the oxidation of 5-amino-1-(2,6-dichloro-4-trifluoromethylphenyl)-3-cyano-4-trifluoromethylthiopyrazole is the co-formation of the corresponding sulfone compound 5-amino-1-(2,6-dichloro-4-trifluoromethylphenyl)-3-cyano-4-trifluoromethylsulfonylpyrazole, which is difficult to remove from the sulfoxide. A number of oxidants (including among others sodium vanadate, sodium tungstate, peracetic acid, performic acid and pertrichloroacetic acid) have been employed in an attempt to obtain an efficient and regioselective oxidation which will provide 5-amino-1-(2,6-dichloro-4-trifluoromethylphenyl)-3-cyano-4-trifluoromethylsulfinylpyrazole in pure form and which may also be utilized for large scale preparations. All of the above methods were found to be unsatisfactory in one respect or another.

It has now been found that a mixture of trifluoroacetic acid and hydrogen peroxide (trifluoroperacetic acid) gives excellent results in terms of both selectivity and yield.

However a problem of using the trifluoroacetic acid and hydrogen peroxide mixture on large scales is that it leads to corrosion of the glass linings of industrial reaction vessels, which is rapid (typically 300 $\mu$m/year) even at ambient temperatures, while at 80° C. the speed of corrosion increases to about 1430 $\mu$m/year. This corrosion occurs as a result of the formation of hydrogen fluoride, and therefore prohibits the use of this reagent mixture in such vessels.

It has now been found that the addition of a corrosion inhibiting compound such as boric acid to the reaction mixture inhibits the corrosion process and reduces the speed of corrosion to a level that is typically less than 5 $\mu$m/year.

European Patent Publication No. 0374061 and J-L. Clavel et al. in *J. Chem. Soc. Perkin I*, (1992), 3371–3375 describe the preparation of 5-amino-1-(2,6-dichloro-4-trifluoromethylphenyl)-3-cyanopyrazol-4-yl disulfide, and the further conversion of this disulfide to the pesticidally active 5-amino-1-(2,6-dichloro-4-trifluoromethylphenyl)-3-cyano-4-trifluoromethylthiopyrazole by reaction with trifluoromethyl bromide in the presence of sodium formate and sulfur dioxide in N,N-dimethylformamide in an autoclave at low pressure (typically 13 bars) at 60° C.

However on larger scales the reaction is very exothermic which results in a substantial pressure increase in the vessel and associated operator hazard.

Moreover it is necessary to add the trifluoromethyl bromide quickly (generally within 0.5 hour), because the mixture of disulfide, sodium formate, sulfur dioxide and N,N-dimethylformamide has been found to be unstable (typically leading to 55% degradation into unwanted by-products within 2 hours at 50° C.). This requirement for rapid addition of trifluoromethyl bromide is not compatible with the exothermic nature of the reaction.

In order to overcome these problems and develop a process which can be used on a large scale other conditions have been sought.

In the above described procedures the reaction was performed by addition of the trifluoromethyl bromide to a mixture of the other components. A new process has now been developed in which the order of addition is different.

European Patent Publication No. 0374061 describes the preparation of 5-amino-1-(2,6-dichloro-4-trifluoromethylphenyl)-3-cyanopyrazol-4-yl disulfide by the reaction of 5-amino-1-(2,6-dichloro-4-trifluoromethylphenyl)-3-cyano-4-thiocyanatopyrazole with base, and the further conversion of this disulfide to the pesticidally active 5-amino-1-(2,6-dichloro-4-trifluoromethylphenyl)-3-cyano-4-trifluoromethylthiopyrazole.

European Patent Publication No. 0295117 discloses a process for the preparation of 1-aryl-3,5-disubstituted-pyrazol-4-yl disulfides by the hydrolysis of the corresponding 4-thiocyanatopyrazole derivatives using hydrochloric acid in ethanol, or by reduction using sodium borohydride in ethanol, or by treatment with aqueous sodium hydroxide under phase transfer conditions in the presence of chloroform and benzyltriethylammonium chloride.

The preparation of the above 5-amino-1-aryl-3-cyano-4-thiocyanatopyrazole intermediates is also described in European Patent Publication Numbers 0374061 and 0295117, and these are obtained by the thiocyanation of the corresponding 5-amino-1-aryl-3-cyanopyrazole derivatives using an alkali metal or ammonium thiocyanate in the presence of bromine and methanol at low temperature.

The above 2-step process for the preparation of 5-amino-1-aryl-3-cyanopyrazol-4-yl disulfide intermediates from 5-amino-1-aryl-3-cyanopyrazoles presents several problems which limit its usefulness for application on large scales:

i) the thiocyanation step is generally performed at very low temperatures, ii) the mixture of bromine and methanol used in the thiocyanation reaction may form explosive mixtures, iii) the above reactions involve heterogeneous mixtures, and iv) it is difficult to obtain complete transformations to product in either reaction stage.

In order to overcome these problems other conditions have been sought. Thus the explosive hazard may be avoided in the thiocyanation reaction by replacing the methanol with a mixture of dichloromethane and water, however this procedure is not efficient on large scales.

The thiocyanation reaction may alternatively be successfully carried out using an alkali metal or ammonium thiocyanate in the presence of hydrogen peroxide and a mineral acid such as hydrochloric acid in a solvent such as an alcohol for example methanol. An improved procedure for the subsequent hydrolysis step has been found which involves the use of a base such as an alkali metal hydroxide, for example sodium hydroxide, in the presence of formaldehyde and a solvent such as aqueous methanol, however the disulfide thus obtained is very powdery and difficult to filter. Furthermore in order to obtain the above disulfide in satisfactory quality it is necessary to subject the starting material 5-amino-1-aryl-3-cyanopyrazole to additional purification before it is used in the thiocyanation and hydrolysis reactions.

Hence it may be appreciated that the above 2-step procedure is inefficient for an industrial process, and a single step method lacking these disadvantages would clearly be preferred.

The present invention seeks to provide improved or more economical methods for the preparation of pesticides.

It is a first object of the present invention to provide a convenient process for preparing 5-amino-1-aryl-3-cyano-4-trifluoromethylsulfinylpyrazole pesticides, which are obtained in high yield and high purity.

It is a further object of the present invention to provide a process for preparing 5-amino-1-aryl-3-cyano-4-trifluoromethylsulfinylpyrazole pesticides which is simple and safe to perform, and which results in minimal vessel corrosion.

It is a further object of the present invention to provide a process for the preparation of 5-amino-1-aryl-3-cyano-4-trifluoromethylsulfinylpyrazole pesticides which includes an efficient recovery procedure for the trifluoroacetic acid.

It is a further object of the present invention to provide a convenient process for preparing 5-amino-1-aryl-3-cyano-4-trifluoromethylthiopyrazole pesticides and pesticidal intermediates, which are obtained in high yield and high purity with improved transformation of the 5-amino-1-aryl-3-cyanopyrazol-4-yl disulfide.

It is a further object of the present invention to provide a process for preparing 5-amino-1-aryl-3-cyano-4-trifluoromethylthiopyrazole pesticides and pesticidal intermediates, which is simple and safe to perform, is operated at lower pressures and temperatures, and in which side reactions are minimized.

It is a further object of the present invention to provide a convenient process for preparing 5-amino-1-aryl-3-cyanopyrazol-4-yl disulfide pesticidal intermediates, which are obtained in high yield and high purity.

It is a further object of the present invention to provide a single step process for preparing 5-amino-1-aryl-3-cyanopyrazol-4-yl disulfide pesticidal intermediates from 5-amino-1-aryl-3-cyanopyrazole intermediates.

It is a further object of the present invention to provide a process for preparing 5-amino-1-aryl-3-cyanopyrazol-4-yl disulfide pesticidal intermediates which is simple and safe to perform, utilizes readily available materials, allows efficient isolation of the product and does not require additional purification of the 5-amino-1-aryl-3-cyanopyrazole starting material.

It is a further object of the present invention to provide a convenient process for preparing 5-amino-1-aryl-3-cyano-4-trifluoromethylsulfinylpyrazole pesticides by a three step process starting from 5-amino-1-aryl-3-cyanopyrazoles.

These and other objects of the invention will become apparent from the following description, and are achieved in whole or in part by the present invention.

According to a feature of the present invention there is provided an improved process (A) for the preparation of a compound of formula (I):

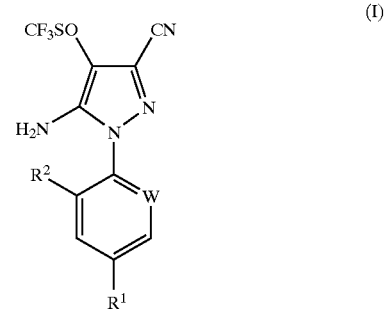

(I)

wherein W represents nitrogen or —CR$^3$;

R$^1$ represents halogen, haloalkyl (preferably trifluoromethyl), haloalkoxy (preferably trifluoromethoxy), R$^4$S(O)$_n$—, or —SF$_5$;

R$^2$ represents hydrogen or halogen (for example chlorine or bromine);

R$^3$ represents halogen (for example chlorine or bromine);

R$^4$ represents alkyl or haloalkyl; and n represents 0, 1 or 2; which process comprises oxidizing a compound of formula (II):

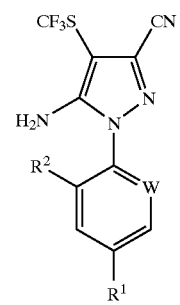

(II)

wherein R$^1$, R$^2$ and W are as hereinbefore defined, with trifluoroperacetic acid in the presence of a corrosion inhibiting compound.

In a preferred embodiment of the invention the trifluoroperacetic acid is generated in situ by the reaction of trifluoroacetic acid and hydrogen peroxide. Accordingly, this embodiment comprises treating a compound of formula (II) as defined above with trifluoroacetic acid and hydrogen peroxide.

Unless otherwise specified in the present specification 'alkyl' means straight- or branched-chain alkyl having from one to six carbon atoms (preferably one to three). Unless otherwise specified 'haloalkyl' and 'haloalkoxyl' are straight- or branched-chain alkyl or alkoxy respectively having from one to six carbon atoms (preferably one to three) substituted by one or more halogen atoms selected from fluorine, chlorine and bromine.

When R$^1$ represents R$^4$S(O)$_n$— and n is 0 or 1, the process may bring about oxidation to the corresponding compound in which n is 1 or 2, respectively.

The corrosion inhibiting compound is generally boric acid or an alkali metal borate such as sodium borate; or any hydrogen fluoride trapping agent such as silica (silicon dioxide), optionally in the form of silica oil. Preferably the corrosion inhibiting compound is boric acid.

The amount of corrosion inhibiting compound used is generally 0.08–0.22 molar equivalents, and preferably about 0.08–0.1 molar equivalents.

The amount of trifluoroacetic acid employed is generally from 14–15 molar equivalents.

The amount of hydrogen peroxide influences the reaction since an excess will lead to the formation of the corresponding sulfone of the compound of formula (I), while a deficiency will lead to incomplete transformation, and in either event an impure final product is obtained. Thus the amount of hydrogen peroxide used in the reaction (generally as a 35% aqueous solution) is generally from 1.3–1.5 equivalents, preferably about 1.31–1.35 equivalents and more preferably about 1.33 equivalents.

The reaction is generally performed at a temperature of from 10–15° C. and preferably at about 12° C.

A further problem associated with the use of trifluoroacetic acid and hydrogen peroxide concerns the recovery and recycling of the expensive trifluoroacetic acid which is essential for the operation of an economically efficient process. In one procedure that was developed in an attempt to solve this problem, the reaction mixture was quenched with sulfur dioxide and a part of the trifluoroacetic acid removed by distillation. An excess of ethanol was then added to the residue to form ethyl trifluoroacetate which was then removed by distillation. The product was then crystallized from a mixture of ethanol/water. This procedure was found to have two disadvantages:

i) the ethanol/water mixture does not provide sufficiently pure 5-amino-1-(2,6-dichloro-4-trifluoromethylphenyl)-3-cyano-4-trifluoromethylsulfinylpyrazole; and ii) the recycling of trifluoroacetic acid via the acid hydrolysis of ethyl trifluoroacetate is a complex process on a large scale and generates a large quantity of unwanted sodium sulfate thus presenting a waste problem.

A new procedure has now been found which solves both of these problems and thus provides a simple and efficient method for the preparation of 5-amino-1-(2,6-dichloro-4-trifluoromethylphenyl)-3-cyano-4-trifluoromethylsulfinylpyrazole in high yield and purity, and in addition provides an efficient recovery procedure for trifluoroacetic acid. In this process, when the reaction in trifluoroacetic acid and hydrogen peroxide is judged to be complete, the excess of hydrogen peroxide is generally quenched with sulfur dioxide (or equivalent reagent), chlorobenzene is added and the trifluoroacetic acid removed by distillation. Typically the trifluoroacetic acid is removed by azeotropic distillation under reduced pressure. An alcohol such as methanol, ethanol or isopropanol (preferably ethanol) is then added to the residue and warmed to about 80° C. until a solution is formed, and then cooled to about 40° C. when the 5-amino-1-(2,6-dichloro-4-trifluoromethylphenyl)-3-cyano-4-trifluoromethylsulfinylpyrazole crystallizes. The alcohol is evaporated at 40° C. under reduced pressure, the mixture cooled to about 0° C., filtered, and the product washed and dried in vacuo. Chlorobenzene has been found to be the only industrial solvent which is compatible with the mixture, has a boiling point significantly higher than that of trifluoroacetic acid, and allows crystallization of 5-amino-1-(2,6-dichloro-4-trifluoromethylphenyl)-3-cyano-4-trifluoromethylsulfinylpyrazole in good yield and quality.

Thus a preferred aspect of the process of the invention as described above further comprises adding chlorobenzene to the reaction mixture on completion of the oxidation reaction, and recovering the trifluoroacetic acid by distillation.

According to a further feature of the present invention there is provided an improved process (B) for the preparation of a compound of formula (II) as defined above; which process comprises the addition of sulfur dioxide to a mixture comprising a disulfide of formula (III):

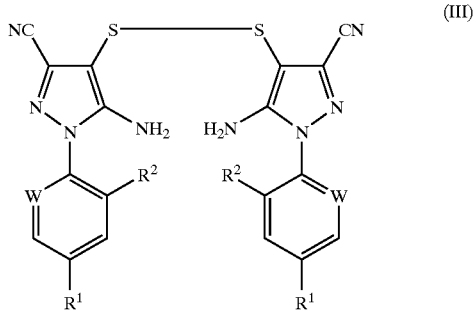

(III)

wherein $R^1$, $R^2$ and W are as hereinbefore defined, a formate salt, trifluoromethylbromide and a polar solvent. The polar solvent is generally selected from N,N-dimethylformamide, N,N-dimethylacetamide, N-methylpyrrolidinone, dimethylsulfoxide, sulfolane, hexamethylphosphoramide and ethers such as dioxan, tetrahydrofuran and dimethoxyethane. It is preferably N,N-dimethylformamide, N,N-dimethylacetamide, N-methylpyrrolidinone, dimethylsulfoxide or sulfolane, more preferably N,N-dimethylformamide.

The advantages of performing the process with this order of addition are:

i) the mixture of disulfide of formula (III), sodium formate, trifluoromethyl bromide and polar solvent (preferably N,N-dimethylformamide) is stable and so the sulfur dioxide may be added more slowly without risk of degradation, thus providing a more convenient and safe process, ii) the new process is efficient being characterized by good yields of product and high transformation of disulfide, and iii) the rate of addition of sulfur dioxide may be controlled so that any increase in the reaction temperature and/or pressure can be maintained at a safe level, thus allowing large scale reactions to be performed safely (including for example typical commercial reactors having about 15 m³ volume).

The formate salt is generally an alkali metal or ammonium salt, preferably sodium formate.

The reaction temperature during the addition of the sulfur dioxide is generally from 35–55° C., preferably from about 35–50° C., most preferably from about 43–47° C., which allows efficient control of the heat from the exothermic reaction. Below 35° C. the reaction tends to proceed too slowly to be useful for an industrial process. At temperatures above 55° C. the yield and quality of product is reduced.

The sulfur dioxide is generally added at such a rate that the temperature is maintained within the above defined range. On large scales this is generally carried out over a 0.5–2 hour period, preferably during about 1–1.5 hours. An addition time of about 1–1.5 hours has been shown to be optimal in minimizing the formation of by-products.

The molar ratio of trifluoromethyl bromide:disulfide of formula (III) is preferably from 3:1 to 5:1. It is convenient to employ a molar ratio of about 3:1.

The amount of sulfur dioxide used is generally from 1.2–1.5 molar equivalents relative to the disulfide of formula (III) and preferably about 1.3 molar equivalents. When only 1 equivalent is employed the yield of product is lowered and transformation of disulfide tends to be incomplete, while an excess of sulfur dioxide leads to degradation during evaporation of the solvent in the work-up.

The amount of formate salt used is generally 4–6 molar equivalents relative to the disulfide of formula (III), preferably about 4.5–5.5 molar equivalents. A joint reduction in the amount of sulfur dioxide and formate salt can be made until the ratio of sulfur dioxide:disulfide is from about 1.2:1 and the ratio of formate salt:disulfide is from about 4.5:1.

By using the process according to the above description the pressure in the vessel is generally easily maintained in the safe range of 3–6 bars.

According to a further feature of the present invention there is provided a process (C) for the preparation of a disulfide of formula (III) as defined above; which comprises adding sulfur monochloride ($S_2Cl_2$) to a solution in an organic solvent of a compound of formula (IV):

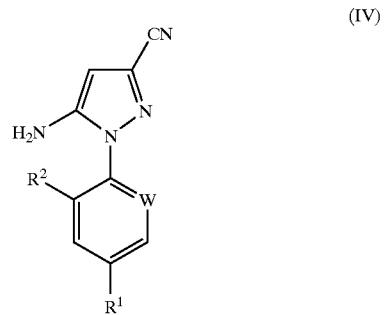

(IV)

wherein $R^1$, $R^2$ and W are as hereinbefore defined.

The reaction is preferably conducted in a solvent selected from toluene, dichloromethane or dichloroethane, or aliphatic or aromatic nitriles such as acetonitrile, propionitrile, methylglutaronitrile and benzonitrile; or mixtures thereof, optionally as a mixture with chlorobenzene (which is present when a chlorobenzene solution of the compound of formula (IV) obtained from the previous reaction stage is used). Acetonitrile optionally in the presence of chlorobenzene is the preferred solvent for the reaction. The reaction is very sensitive to the effect of solvent and while it may be convenient to use toluene since a toluene solution of (IV) may be available from the previous reaction stage, a significant amount of the monosulfide (V):

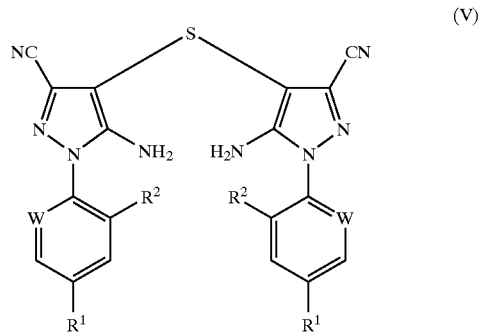

(V)

is generally formed as a by-product when these conditions are employed. Moreover the product is very slow to filter when toluene is employed, although an acceptable filtration rate may be obtained by addition of a proportion of acetonitrile to the toluene solution. When the reaction is performed in the preferred solvent acetonitrile, the amount of monosulfide impurity (V) is reduced and the rate of filtration of the product (III) is satisfactory.

The sulfur monochloride used in the process is generally from 99.4–99.9% w/w pure.

The quality of solvent used may affect the reaction since the presence of certain impurities can influence the yield of product (with the formation of (V) as by-product). Thus when acetonitrile is employed as solvent it is preferred that the content of water is <1000 ppm, the content of ethanol is <1500 ppm and the content of ammonia is <100 ppm. It is also preferable to avoid the presence of even low amounts of acetone or N,N-dimethylformamide in the solvent mixture since, for example, the presence of about 100 ppm of acetone in dichloromethane may have a negative impact on the yield of product.

The order of addition of the reagents is an important feature of the reaction. Thus it is very important to add the sulfur monochloride to a solution of compound of formula (IV) (rather than the reverse). A rapid addition time for the sulfur monochloride is a preferred feature of the process. Thus if the sulfur monochloride is added during 1 minute, the disulfide (III) crystallizes about 15 seconds after the completion of the addition (and all of the compound of formula (IV) has been consumed). When added over a 15 minute period the disulfide (III) crystallizes in mid-addition and as a result the disulfide (III) co-crystallizes with the remaining compound of formula (IV). Washing the impure product so obtained with a large excess of acetonitrile does not effect removal of the unreacted compound of formula (IV). The time for the sulfur monochloride addition is preferably from 1–10 minutes, more preferably about 1–5 minutes.

The reaction temperature of the mixture at the start of the addition of the sulfur monochloride is preferably from 5 to 25° C., more preferably from about 10 to 20° C. If the temperature is at 30° C. at the start of the addition, a lower yield is obtained due to the formation of trisulfide and tetrasulfide by-products. As the reaction is exothermic the temperature increases during the reaction and is preferably held at from about 20 to 35° C.

The molar ratio of compound of formula (IV):sulfur monochloride used in the reaction is generally from 2:1 to 2:1.06, and preferably from about 2:1 to about 2:1.04. Using a larger excess of sulfur monochloride results in the formation of an increased amount of the monosulfide by-product (V). If a lower proportion of sulfur monochloride is used the reaction does not proceed to completion.

A further feature of the process of the invention is the method used for the purification of the product. Thus the reaction mixture containing the disulfide of formula (III) is first degassed to remove hydrogen chloride, generally by heating at about 40° C. under reduced pressure, generally at about 0.2 atmosphere. It is then heated at about 80° C. for about 1 hour at atmospheric pressure. After cooling to about 30° C., a weak base (generally ammonia) is added to neutralize any remaining hydrogen chloride and obtain a pH of about 6.5–7. The mixture is then cooled to about 5° C. and the product isolated by filtration. This procedure enables the disulfide of formula (I) to be obtained in high yield and purity by a simple procedure convenient for large scale operations.

In formulae (I), (II), (III) and (IV), preferred values of the symbols are as follows:

R[1] represents haloalkyl (preferably trifluoromethyl), haloalkoxy (preferably trifluoromethoxy) or —SF$_5$;

W represents —CR[3];

R[2] and R[3] represent halogen (preferably chlorine).

A particularly preferred compound of formula (I) is:
5-amino-1-(2,6-dichloro-4-trifluoromethylphenyl)-3-cyano-4-trifluoromethylsulfinylpyrazole.

A particularly preferred compound of formula (II) is:
5-amino-1-(2,6-dichloro-4-trifluoromethylphenyl)-3-cyano-4-trifluoromethylthiopyrazole.

A particularly preferred compound of formula (III) is:
5-amino-1-(2,6-dichloro-4-trifluoromethylphenyl)-3-cyanopyrazol-4-yl disulfide.

Compounds of formulae (II), (III) and (IV) are known.

According to a further feature of the present invention the processes (A), (B) and (C) can be combined to prepare a compound of formula (I) from a compound of formula (IV).

The above processes (A), (B) and (C) when combined together form a particularly useful and efficient method for the preparation of Fipronil.

The following non-limiting examples illustrate the invention.

EXAMPLE 1

Preparation of 5-amino-1-(2,6-dichloro-4-trifluoromethylphenyl)-3-cyano-4-trifluoromethylsulfinylpyrazole Trifluoroacetic acid (1660 g, 14.5 mol) was added to a stirred solution of 5-amino-1-(2,6-dichloro-4-trifluoromethylphenyl)-3-cyano-4-trifluoromethylthiopyrazole (436 g, 1.03 mol) and boric acid (5 g, 0.08 mol) in a glass reactor at 12° C. Hydrogen peroxide (131.5 g of 35% w/w, 1.35 mol) was added over 2 hours while maintaining the temperature at 12° C., and the mixture kept at this temperature for a further 4–5 hours. When the transformation had reached 97–98%, or the amount of unwanted 5-amino-1-(2,6-dichloro-4-trifluoromethylphenyl)-3-cyano-4-trifluoromethylsulfonylpyrazole reached 2% (as judged by HPLC analysis), sulfur dioxide was added to quench any remaining hydrogen peroxide, and the mixture maintained at 10–18° C. for 0.5 hour. Chlorobenzene (370 g) was added and the mixture placed under reduced pressure (from 0.17 to 0.04 atmospheres) and heated to 47–50° C. with azeotropic distillation. A homogeneous fraction containing recovered trifluoroacetic acid was obtained. During the distillation additional chlorobenzene (1625 g) was added continuously in order to maintain a constant volume. At the end of the azeotropic distillation the reactor contents were maintained at 47–50° C. under reduced pressure (0.04 atmosphere), and a homogeneous fraction of chlorobenzene distilled. After release of the vacuum, the reactor was heated to 40° C., ethanol (207 g) and chlorobenzene (235 g) added, and the mixture heated to 80° C. with stirring to give a solution. On cooling to 40° C. the product crystallized. The reactor was placed under progressively reduced pressure (from 0.13 to 0.03 atmosphere) and the ethanol distilled at 40° C. The vacuum was released and the mixture cooled to 5° C. during 3.5 hours and left for a further 0.5 hour. The product was filtered off, washed with cold chlorobenzene, then with cold aqueous ethanol, then with water, and dried in vacuo at 135° C. to give the title compound (407.5 g), in a typical yield of 89% and purity of 95.5%.

EXAMPLE 2

Preparation of 5-amino-3-cyano-1-(2,6-dichloro-4-trifluoromethylphenyl)-4-trifluoromethylthiopyrazole Sodium formate (76 g, 1.11 mol) was added to a mixture of 5-amino-1-(2,6-dichloro-4-trifluoromethylphenyl)-3-cyanopyrazol-4-yl disulfide (157.5 g, 0.223 mol) and N,N-dimethylformamide (643 g) in a glass reactor. After purging with nitrogen at 2 bars, the reactor was sealed and trifluoromethyl bromide (101 g, 0.682 mol) added. The reactor was heated to 45° C. and sulfur dioxide (19.5 g, 0.304 mol) added over 1.5 hours and the temperature maintained between 43° C. and 47° C. during the reaction and for a further 0.75 hour. The pressure was released to effect degassing for 1.5 hours, with cooling of the vessel to 25–30° C. 1 hour after the release of pressure. When the internal pressure reached atmospheric pressure the mixture was treated with sodium bicarbonate and the N,N-dimethylformamide partially evaporated while heating to 50–70° C. at reduced pressure. The residue was cooled to 40° C. and added slowly to water with stirring at 20–25° C. The product was filtered, washed (hot water) and dried in vacuo at 100° C. to give the title compound (182.3 g) in typical yields of 95% and purity of 96.6%.

EXAMPLE 3

Preparation of 5-amino-1-(2,6-dichloro-4-trifluoromethylphenyl)-3-cyanopyrazol-4-yl disulfide Acetonitrile (837 g) was added to a chlorobenzene solution (627.8 g) which contained 5-amino-1-(2,6-dichloro-4-trifluoromethylphenyl)-3-cyanopyrazole (366.6 g. 1.14 mol). The mixture was heated at 50–64° C. under reduced pressure (0.5 atmosphere) and dried by the distillation of about 45 ml of the acetonitrile. After cooling to 18° C., sulfur monochloride (77 g, 0.57 mol) was added rapidly over 1 minute. The temperature of the mixture increased to 35° C. and was maintained at 35° C. by cooling until the exotherm ceased and for a further 0.3 hour. The mixture was then degassed (to remove hydrogen chloride) by heating at 40° C. under reduced pressure, and then heated at 80° C. for 1 hour at atmospheric pressure. After cooling to 30° C., ammonia was added to bring the pH to 6.5–7, cooled to 5° C. and the product filtered off, washed with chlorobenzene/acetonitrile and dried at 95° C. under vacuum to give the title compound (365.2 g) in typical yield of 89.4% and 98.4% purity.

What is claimed is:

1. A process (B) for the preparation of a compound having the formula (II):

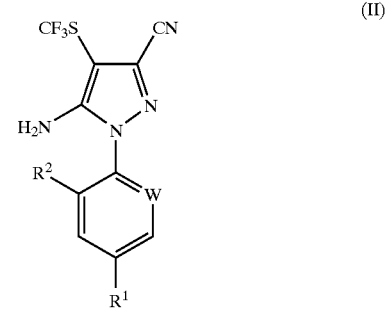

wherein:

W is —CR[3];

R[1] is halogen, haloalkyl, or haloalkoxy;

R[2] is hydrogen or halogen; and

R[3] is halogen;

said process comprising adding sulfur dioxide to a mixture comprising a disulfide having the formula (III):

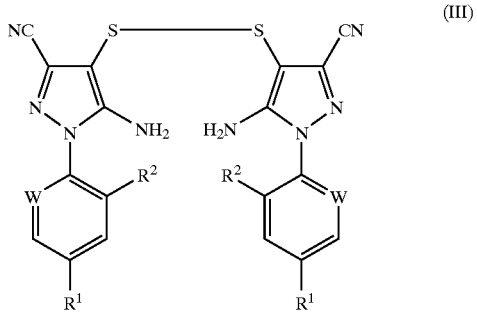

wherein $R^1$, $R^2$ and W are as defined above, a formate salt, trifluoromethyl bromide and a polar solvent.

2. A process according to claim 1, wherein the solvent is N,N-dimethylformamide.

3. A process according to claim 1, wherein the reaction temperature during the addition of the sulfur dioxide is from about 35° C. to about 55° C.

4. A process according to claim 2, wherein the reaction temperature during the addition of the sulfur dioxide is from about 35° C. to about 55° C.

5. A process according to claim 1, wherein the sulfur dioxide is added over a period of from about 0.5 to about 2 hours.

6. A process according to claim 2, wherein the sulfur dioxide is added over a period of from about 0.5 to about 2 hours.

7. A process according to claim 3, wherein the sulfur dioxide is added over a period of from about 0.5 to about 2 hours.

8. A process according to claim 4, wherein the sulfur dioxide is added over a period of from about 0.5 to about 2 hours.

9. A process according to claim 1, wherein the molar ratio of trifluoromethyl bromide to disulfide of formula (III) is from about 3:1 to about 5:1.

10. A process according to claim 2, wherein the molar ratio of trifluoromethyl bromide to disulfide of formula (III) is from about 3:1 to about 5:1.

11. A process according to claim 3, wherein the molar ratio of trifluoromethyl bromide to disulfide of formula (III) is from about 3:1 to about 5:1.

12. A process according to claim 5, wherein the molar ratio of trifluoromethyl bromide to disulfide of formula (III) is from about 3:1 to about 5:1.

13. A process according to claim 7, wherein the molar ratio of trifluoromethyl bromide to disulfide of formula (III) is from about 3:1 to about 5:1.

14. A process according to claim 1, wherein the amount of sulfur dioxide employed is from about 1.2 to about 1.5 molar equivalents relative to the disulfide of formula (III).

15. A process according to claim 2, wherein the amount of sulfur dioxide employed is from about 1.2 to about 1.5 molar equivalents relative to the disulfide of formula (III).

16. A process according to claim 3, wherein the amount of sulfur dioxide employed is from about 1.2 to about 1.5 molar equivalents relative to the disulfide of formula (III).

17. A process according to claim 5, wherein the amount of sulfur dioxide employed is from about 1.2 to about 1.5 molar equivalents relative to the disulfide of formula (III).

18. A process according to claim 1, wherein the formate salt is an alkali metal or ammonium formate.

19. A process according to claim 2, wherein the formate salt is an alkali metal or ammonium formate.

20. A process according to claim 3, wherein the formate salt is an alkali metal or ammonium formate.

21. A process according to claim 5, wherein the formate salt is an alkali metal or ammonium formate.

22. A process according to claim 18, wherein the formate salt is sodium formate.

23. A process according to claim 19, wherein the formate salt is sodium formate.

24. A process according to claim 20, wherein the formate salt is sodium formate.

25. A process according to claim 21, wherein the formate salt is sodium formate.

26. A process according to claim 1, wherein the amount of formate salt employed is from about 4 to about 6 molar equivalents relative to the disulfide of formula (III).

27. A process according to claim 2, wherein the amount of formate salt employed is from about 4 to about 6 molar equivalents relative to the disulfide of formula (III).

28. A process according to claim 3, wherein the amount of formate salt employed is from about 4 to about 6 molar equivalents relative to the disulfide of formula (III).

29. A process according to claim 1, wherein the disulfide of formula (III) is 5-amino-1-(2,6-dichloro-4-trifluoromethylphenyl)-3-cyanopyrazol-4-yl disulfide and the compound of formula (II) is 5-amino-1-(2,6-dichloro-4-trifluoromethylphenyl)-3-cyano-4-trifluoromethylthiopyrazole.

30. A process (B) for the preparation of a compound having the formula (II):

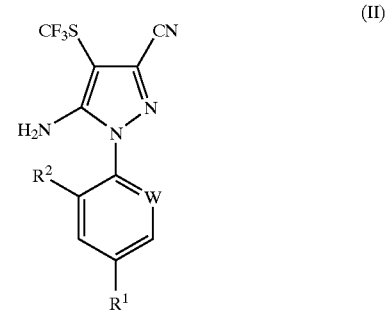

wherein:
W is —CR³;
$R^1$ is halogen, haloalkyl, or haloalkoxy;
$R^2$ is hydrogen or halogen; and
$R^3$ is halogen;
said process comprising adding sulfur dioxide to a mixture comprising a disulfide having the formula (III):

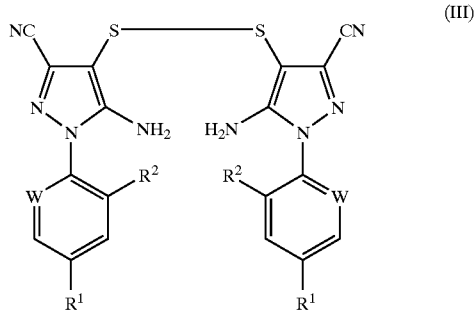

wherein $R^1$, $R^2$ and W are as defined above, sodium formate, trifluoromethyl bromide and N,N- dimethylformamide, the reaction temperature during the addition of the sulfur dioxide being from about 35° C. to about 55° C., the sulfur dioxide being added over a period of from about 0.5 to about 2 hours, the molar ratio of trifluoromethyl bromide to disulfide of formula (III) being from about 3:1 to about 5:1, the amount of sulfur dioxide employed being from about 1.2 to about 1.5 molar equivalents relative to the disulfide of formula (III) and the amount of sodium formate employed being from about 4 to about 6 molar equivalents relative to the disulfide of formula (III).

31. The process according to claim 30, wherein the disulfide of formula (III) is 5-amino-1-(2,6-dichloro-4-trifluoromethylphenyl)-3-cyanopyrazol-4-yl disulfide and the compound of formula (II) is 5-amino-1-(2,6-dichloro-4-trifluoromethylphenyl)-3-cyano-4-trifluoromethylthiopyrazole.

32. A process for the preparation of a compound having the formula (I):

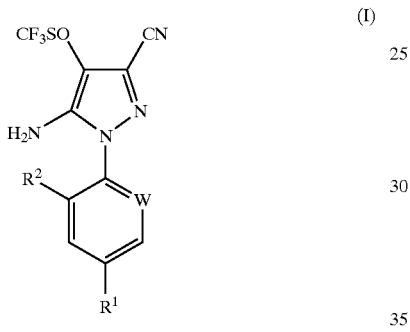

wherein:

W is —CR³;

R¹ is halogen, haloalkyl, or haloalkoxy;

R² is hydrogen or halogen; and

R³ is halogen;

said process comprising:

(a) adding sulfur dioxide to a mixture comprising a disulfide having the formula (III):

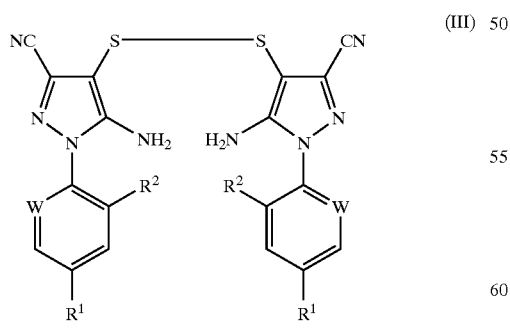

wherein R¹, R² and W are as defined above, a formate salt, trifluoromethyl bromide and a polar solvent, to afford a compound having the formula (II):

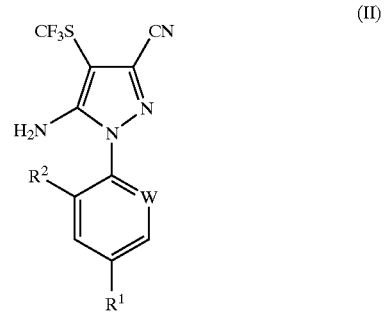

wherein R¹, R² and W are as defined above; and (b) oxidizing the resultant compound of formula (II) with trifluoroperacetic acid in the presence of a corrosion inhibiting compound to afford a compound having the formula (I).

33. A process for the preparation of a compound having the formula (II):

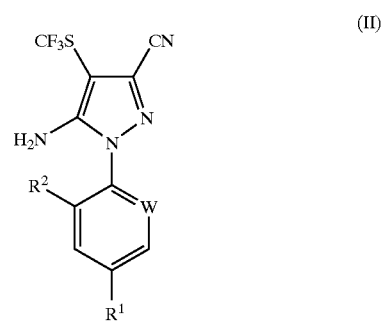

wherein:

W is —CR³;

R¹ is halogen, haloalkyl, or haloalkoxy;

R² is hydrogen or halogen; and

R³ is halogen;

said process comprising:

(a) adding sulfur monochloride (S₂Cl₂) to a solution, in an organic solvent, of a compound having the formula (IV):

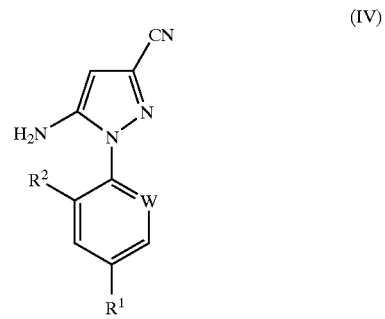

wherein R¹, R² and W are as defined above, to afford a disulfide having the formula (III):

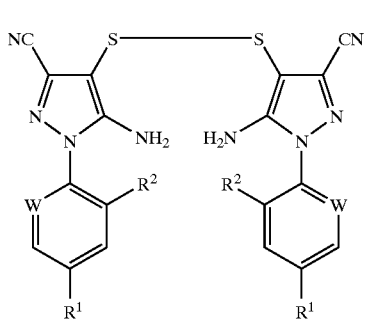

(III)

wherein R¹, R² and W are as defined above; and (b) adding sulfur dioxide to a mixture comprising the resultant disulfide having formula (III), a formate salt, trifluoromethyl bromide and a polar solvent, to afford a compound having the formula (II).

34. A process according to claim 33, wherein the compound of formula (IV) is 5-amino-1-(2,6-dichloro-4-trifluoromethylphenyl)-3-cyanopyrazole, the disulfide of formula (III) is 5-amino-1-(2,6-dichloro-4-trifluoromethylphenyl)-3-cyanopyrazol-4-yl disulfide and the compound of formula (II) is 5-amino-1-(2,6-dichloro-4-trifluoromethylphenyl)-3-cyano-4-trifluoromethylthiopyrazole.

35. A process for the preparation of a compound having the formula (I):

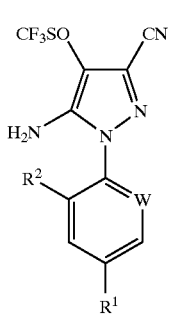

(I)

wherein W is —CR³;

R¹ is halogen, haloalkyl, or haloalkoxy;

R² is hydrogen or halogen; and

R³ is halogen;

said process comprising:

(a) adding sulfur monochloride (S₂Cl₂) to a solution, in an organic solvent, of a compound having the formula (IV):

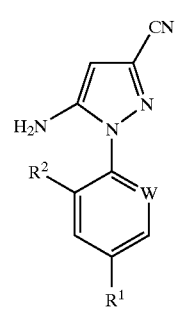

(IV)

wherein R¹, R² and W are as defined above, to afford a disulfide having the formula (III):

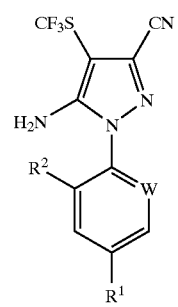

(III)

wherein R¹, R² and W are as defined above;

(b) adding the sulfur dioxide to a mixture comprising the resultant disulfide having the formula (III), a formate salt, trifluoromethyl bromide and a polar solvent, to afford a compound having the formula (II):

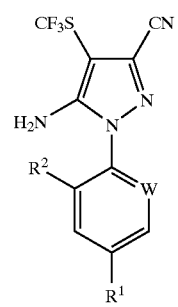

(II)

wherein R¹, R² and W are as defined above; and (c) oxidizing the resultant compound having the formula (II) with trifluoroperacetic acid in the presence of a corrosion inhibiting compound.

36. A process according to claim 35, wherein the compound of formula (I) is 5-amino-1-(2,6-dichloro-4-trifluoromethylphenyl)-3-cyano-4-trifluoromethylsulfinylpyrazole, the compound of formula (II) is 5-amino-1-(2,6-dichloro-4-trifluoromethylphenyl)-3-cyano-4-trifluoromethylthiopyrazole, the disulfide of formula (III) is 5-amino-1-(2,6-dichloro-4- trifluoromethylphenyl)-3-cyanopyrazol-4-yl disulfide, and the compound of formula (IV) is 5-amino-1-(2,6-dichloro-4-trifluoromethylphenyl)-3-cyanopyrazole.

37. A process according to claim 1, wherein:
$R^1$ is trifluoromethyl, or trifluoromethoxy;
W is —$CR^3$;
$R^2$ is chlorine; and
$R^3$ is chlorine.

38. A process according to claim 30, wherein:
$R^1$ is trifluoromethyl, or trifluoromethoxy;
W is —$CR^3$;
$R^2$ is chlorine; and
$R^3$ is chlorine.

39. A process according to claim 32, wherein:
$R^1$ is trifluoromethyl, or trifluoromethoxy;
W is —$CR^3$;
$R^2$ is chlorine; and
$R^3$ is chlorine.

40. A process according to claim 33, wherein:
$R^1$ is trifluoromethyl, or trifluoromethoxy;
W is —$CR^3$;
$R^2$ is chlorine; and
$R^3$ is chlorine.

41. A process according to claim 35, wherein:
$R^1$ is trifluoromethyl, or trifluoromethoxy;
W is —$CR^3$;
$R^2$ is chlorine; and
$R^3$ is chlorine.

* * * * *